United States Patent
Takizawa et al.

(10) Patent No.: US 9,782,100 B2
(45) Date of Patent: Oct. 10, 2017

(54) BIO-INFORMATION ANALYSIS DEVICE

(71) Applicant: NIHON KOHDEN CORPORATION, Tokyo (JP)

(72) Inventors: Koji Takizawa, Tokyo (JP); Tatsuo Nishihara, Tokyo (JP); Naoki Koura, Tokyo (JP); Yuuho Iwanaga, Tokyo (JP); Naoki Hattori, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/632,340

(22) Filed: Feb. 26, 2015

(65) Prior Publication Data
US 2015/0250400 A1    Sep. 10, 2015

(30) Foreign Application Priority Data
Mar. 10, 2014    (JP) ................. 2014-046925

(51) Int. Cl.
| | | |
|---|---|---|
| A61B 5/00 | (2006.01) | |
| A61B 5/04 | (2006.01) | |
| A61B 5/0452 | (2006.01) | |
| A61N 1/37 | (2006.01) | |
| A61N 1/365 | (2006.01) | |

(52) U.S. Cl.
CPC ...... *A61B 5/04525* (2013.01); *A61B 5/04012* (2013.01); *A61B 5/0452* (2013.01); *A61N 1/365* (2013.01); *A61N 1/3702* (2013.01)

(58) Field of Classification Search
USPC ............................................... 600/509–510
See application file for complete search history.

(56) References Cited

U.S. PATENT DOCUMENTS

| | | | |
|---|---|---|---|
| 5,609,157 A | 3/1997 | Panescu et al. | |
| 2004/0127805 A1 | 7/2004 | MacAdam et al. | |
| 2006/0253044 A1* | 11/2006 | Zhang .................. | A61B 5/7203 600/512 |
| 2008/0188765 A1 | 8/2008 | Stolarski et al. | |
| 2011/0224565 A1* | 9/2011 | Ong ...................... | G06F 19/345 600/509 |
| 2011/0245700 A1 | 10/2011 | Ghanem et al. | |
| 2011/0282226 A1 | 11/2011 | Benser et al. | |
| 2011/0301479 A1* | 12/2011 | Ghanem ............ | A61B 5/04012 600/515 |

(Continued)

FOREIGN PATENT DOCUMENTS

| | | |
|---|---|---|
| JP | 2008-237882 A | 10/2008 |
| JP | 5160245 B2 | 3/2013 |

OTHER PUBLICATIONS

The extended European Search Report for the related European Patent Application Na 15157270.8 dated Aug. 20, 2015.

(Continued)

*Primary Examiner* — Nicole F Johnson
(74) *Attorney, Agent, or Firm* — Kenealy Vaidya LLP (57) ABSTRACT

A bio-information analysis device includes a measuring unit that measures biometric waveforms of a subject, and a calculating unit that calculates a matching rate of the biometric waveforms based on shapes and magnitudes of the biometric waveforms measured by the measuring unit. In the bio-information analysis device, the biometric waveforms may be electrocardiogram waveforms.

12 Claims, 6 Drawing Sheets

(56) References Cited

U.S. PATENT DOCUMENTS

2013/0274582 A1   10/2013   Afonso et al.

OTHER PUBLICATIONS

The European Office Action for the related European Patent Application No. 15157270.8 dated Mar. 13, 2017.
Carmelo Cassisi et al.; "Similarity Measures and Dimensionality Reduction Techniques for Time Series Data Mining"; Advances in Data Mining Knowledge Discovery and Applications; Sep. 12, 2012; XP55287238A.
Japanese Office Action for the related Japanese Patent Application No. 2014-046925 dated May 30, 2017.

* cited by examiner

FIG. 1

FIG. 2A ELECTROCARDIOGRAM WAVEFORM A

FIG. 2B ELECTROCARDIOGRAM WAVEFORM B

FIG. 2C OVERLAPPED WAVEFORMS OF WAVEFORMS A AND B

FIG. 6

BIO-INFORMATION ANALYSIS DEVICE

CROSS REFERENCE TO RELATED APPLICATION

This application is based on Japanese Patent Applications No. 2014-046925 filed on Mar. 10, 2014, the contents of which are incorporated herein by reference.

BACKGROUND

The presently disclosed subject matter relates to a bio-information analysis device for calculating a similarity degree (hereinafter, referred to as a matching rate) between two biometric waveforms.

When an arrhythmia, such as a premature ventricular contraction, is occurred, a treatment of selectively cauterizing an abnormal excitement site corresponding to a cause thereof is known. For this purpose, it is important to exactly identify an occurrence origin of the arrhythmia.

For example, a method of specifying an arrhythmia inducing lesion by recognizing a correlation of a signal waveform of a ventricular tachycardia occurred in a body of a subject and a pace-mapped signal waveform is disclosed from JP5160245.

In the method of specifying according to JP5160245, the legion is specified using a correlation coefficient of biometric waveforms to be compared. However, if shapes in comparison of biometric waveforms are similar to each other, the correlation coefficient exhibits a high value even when magnitudes thereof are different from each other. In this case, a matching rate having a high reliability cannot be obtained and thus an exact occurrence origin of the legion cannot be identified.

Accordingly, the presently disclosed subject matter provides a bio-information analysis device, which can increase reliability of a matching rate of biometric waveforms.

(1) According to an aspect of the presently disclosed subject matter, a bio-information analysis device includes a measuring unit that measures biometric waveforms of a subject, and a calculating unit that calculates a matching rate of the biometric waveforms based on shapes and magnitudes of the biometric waveforms measured by the measuring unit.

According to this configuration (1), magnitudes of waveforms as well as shapes of waveforms can be used as indicators to calculate a matching rate of biometric waveforms, thereby increasing reliability of the matching rate.

(2) In the bio-information analysis device according to the configuration (1), the biometric waveforms may be electrocardiogram waveforms.

According to this configuration, a matching rate having a high reliability in comparison of electrocardiogram waveforms can be calculated.

(3) In the bio-information analysis device according to the configuration (2), the electrocardiogram waveforms, from which the matching rate is calculated, may include a first waveform measured when a premature ventricular contraction is occurred and a second waveform measured when a waveform similar to an arrhythmia is artificially occurred by pacing.

According to this configuration (3), an occurrence origin of a premature ventricular contraction can be exactly identified based on the calculated matching rate having a high reliability, thereby allowing an unnecessary cauterization (ablation) to be avoided and also a lesion to be surely cauterized.

(4) In the bio-information analysis device according to the configuration (3), when calculating the matching rate between the first waveform and the second waveform, the matching rate may be calculated in such a manner that a point, at which the highest matching rate is exhibited, of points on the second waveform is overlapped with a highest amplitude point of the first waveform.

According to this configuration (4), an optimal reference point for overlapping in the biometric waveforms can be obtained, and accordingly the matching rate having a higher reliability can be calculated and an occurrence origin of the premature ventricular contraction can be exactly identified.

(5) In the bio-information analysis device according to the configurations (3) or (4), when calculating the matching rate, a waveform component, which is generated upon pacing and corresponds to a stimulation potential, of the second waveform may be excluded.

According to this configuration (5), a waveform component due to a stimulation potential can be excluded from biometric waveforms measured accompanying with pacing, and accordingly the matching rate having a further higher reliability can be calculated and an occurrence origin of the premature ventricular contraction can be exactly identified.

(6) In the bio-information analysis device according to any one of the configurations (3) to (5), upon calculation of a matching rate with respect to magnitudes of the biometric waveforms, a magnitude of a portion, which has a phase reversed relative to that of the first waveform, of the second waveform, may be changed to zero.

According to this configuration (6), a correction in which a magnitude of a portion, which has a reversed phase, of the biometric waveforms is calculated as zero, is performed, and therefore the matching rate having a further higher reliability can be calculated and an occurrence origin of the premature ventricular contraction can be exactly identified.

According to the bio-information analysis device of the presently disclosed subject matter, reliability of a matching rate of biometric waveforms can be increased.

DETAILED DESCRIPTION OF EMBODIMENTS

Examples of embodiments of a bio-information analysis device according to the presently disclosed subject matter will be now described with reference to the accompanying drawings.

Figure 1:
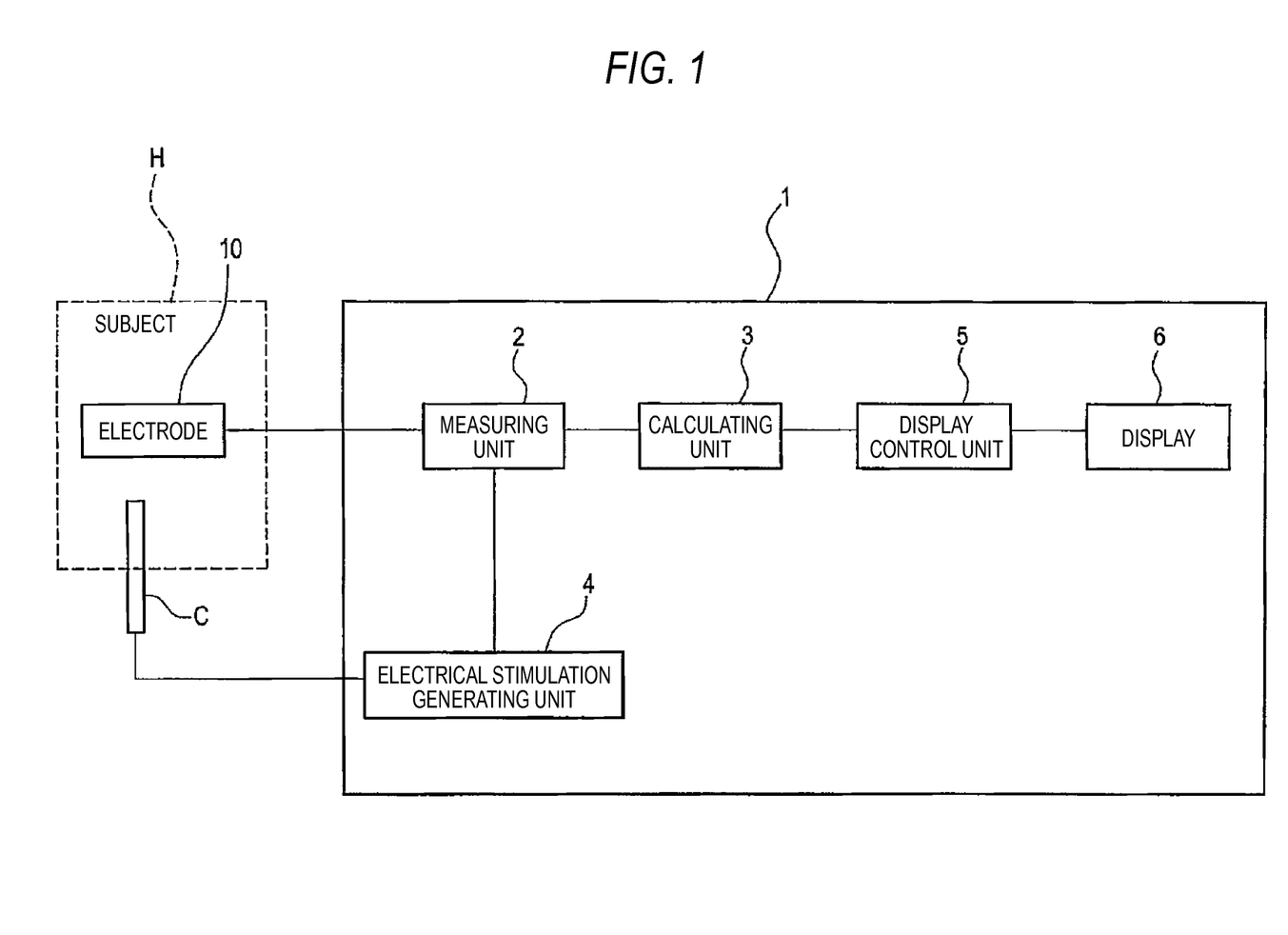
FIG. 1 is a functional block diagram showing a configuration of a bio-information analysis device according to one embodiment of the presently disclosed subject matter.

FIG. 1 is a functional block diagram showing a configuration of a bio-information analysis device 1 according to the present embodiment.

As shown in FIG. 1, the bio-information analysis device 1 includes a measuring unit 2, a calculating unit 3, an electrical stimulation generating unit 4, a display control unit 5 and a display 6.

The bio-information analysis device 1 analyzes bio-information acquired from a subject H. A electrode 10 mounted on the subject H is connected to the bio-information analysis device 1. As the electrode 10, for example, chest electrodes and limb electrodes for measuring a standard 12-lead electrocardiogram, a synthesized 18-lead electrocardiogram or the like are used. Bio-information signals of the subject H detected by the electrode 10 are inputted to the measuring unit 2 of the bio-information analysis device 1.

The measuring unit 2 measures biometric waveforms, e.g., electrocardiogram waveforms, of the subject H based on the bio-information signals inputted from the electrode 10. The measuring unit 2 is connected to the calculating unit 3 and outputs measurement values of the measured biometric waveforms to the calculating unit 3.

The calculating unit 3 calculates a matching rate of the biometric waveforms based on the measurement values of the biometric waveforms inputted from the measuring unit 2. The calculating unit 3 calculates the matching rate of the biometric waveforms based on two indicators including a shape and a magnitude of the biometric waveforms.

The electrical stimulation generating unit 4 generates an electrical stimulation signal for performing pacing. An electrode catheter C for performing pacing is connected to the electrical stimulation generating unit 4. The electrical stimulation signal outputted from the electrical stimulation generating unit 4 is sent to the electrode catheter C. An electrical stimulation is offered from the electrode catheter C, which is inserted into a heart of the subject H, to a myocardium to artificially induce excitement of the myocardium, thereby generating an electrocardiogram waveform. Also, the electrical stimulation generating unit 4 is connected to the measuring unit 2 and outputs a pulse signal, which represents a timing of generating the electrical stimulation signal, to the measuring unit 2. Specifically, the electrode catheter C is put on an inner wall of the heart to apply the electrical stimulation signal, and the measuring unit 2 measures a corresponding electrocardiogram waveform. Stimulating and measuring are repeated while changing sites on which the electrode catheter is put, so that the measured electrocardiogram waveform becomes a waveform similar to an arrhythmia.

The display control unit 5 causes information related to the subject H, such as the measured biometric waveforms and the calculated matching rate of the biometric waveforms, to be displayed on the display 6. The display 6 displays information based on control signals outputted from the display control unit 5. For example, the display 6 is constructed by a liquid crystal screen.

Next, operations of the bio-information analysis device 1 will be described with reference to FIGS. 2A to 6. In this example, operations of calculating a matching rate of electrocardiogram waveforms when a premature ventricular contraction (PVC) or a ventricular tachycardia (VT) is occurred will be described.

Figure 2A:
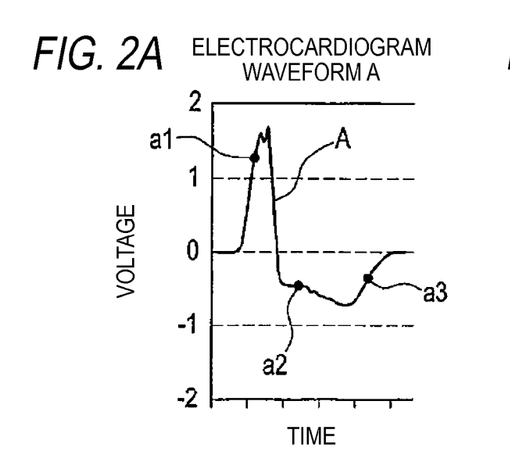
FIG. 2A is a view showing an electrocardiogram waveform when a premature ventricular contraction is actually occurred.

A waveform in FIG. 2A represents an electrocardiogram waveform (an example of a first waveform) A of the subject H when a premature ventricular contraction is actually occurred.

The measuring unit 2 measures the electrocardiogram waveform A based on an electrocardiogram signal detected by the electrode 10. The measuring unit 2 measures six chest lead waveforms (V1 to V6) and six limb lead waveforms (I to III, aVR, aVL, aVF) of the standard 12-lead electrocardiogram via ten electrodes, in total, mounted on six locations on a chest and four locations on limbs of the subject H. The electrocardiogram waveform A represents one of the measured standard 12-lead electrocardiogram waveforms.

Figure 2B:
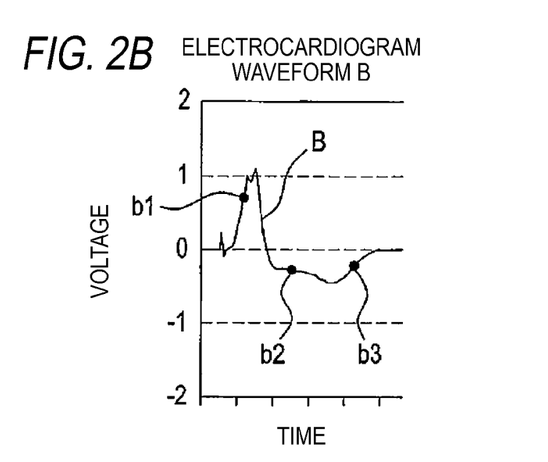
FIG. 2B is a view showing an electrocardiogram waveform when a waveform similar to an arrhythmia is artificially occurred by pacing.

A waveform in FIG. 2B represents an electrocardiogram waveform (an example of a second waveform) B, which is occurred by pacing and similar to an arrhythmia.

The measuring unit 2 measures the electrocardiogram waveform B based on an electrocardiogram signal detected by the electrode 10. The electrode catheter C, which has an electrode at a distal end thereof, is inserted into the heart of the subject H and then an electrical stimulation (pacing) is applied from the distal end of the electrode catheter C to the heart, thereby measuring the electrocardiogram waveform B. The electrocardiogram waveform B is an electrocardiogram waveform measured by a electrode mounted on the same location as that of a electrode measuring the electrocardiogram waveform A in FIG. 2A.

Figure 2C:
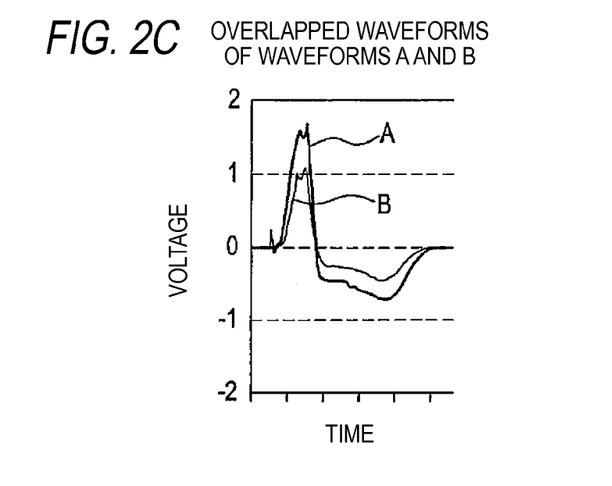
FIG. 2C is a view showing the electrocardiogram waveforms of FIGS. 2A and 2B overlapped with each other.

Waveforms in FIG. 2C is one which the measured electrocardiogram waveform A and electrocardiogram waveform B are overlapped and displayed.

Figure 2D:
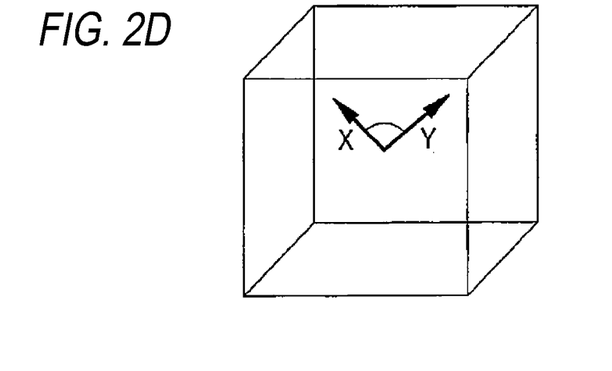
FIG. 2D is a view showing the electrocardiogram waveforms of FIGS. 2A and 2B space-vectorized.

In order to calculate a matching rate of the measured electrocardiogram waveform A and electrocardiogram waveform B, the calculating unit 3 overlaps two waveforms as shown in FIG. 2C and also space-vectorizes waveform data of two waveforms as shown in FIG. 2D. By transposing sample points a1, a2 and a3 of the electrocardiogram waveform A (see FIG. 2A) and sample points b1, b2 and b3 of the electrocardiogram waveform B (see FIG. 2B) into three-dimensional coordinates, the electrocardiogram waveform A and the electrocardiogram waveform B can be represented by space vectors X (a1, a2, a3) and Y (b1, b2, b3). In this example, the vectors are described using three sample points for ease of understanding, but in practice, the vectors are represented by all sample points of both waveforms.

Subsequently, the calculating unit 3 calculates an angle defined by the space vectors X and Y. The angle (radian) defined by the space vectors X and Y can be obtained by the following equation.

$$\text{radian} = \arccos\left\{\frac{a1b1 + a2b2 + a3b3}{\sqrt{(a1)^2 + (a2)^2 + (a3)^2} \sqrt{(b1)^2 + (b2)^2 + (b3)^2}}\right\} \quad \text{[Equation 1]}$$

From a value (0 to 3.14) of the calculated radian, the calculating unit 3 calculates a matching rate by percentage of shapes (vector directions) of the electrocardiogram waveform A and the electrocardiogram waveform B. Here, it should be noted that if radian=0, the matching rate is 100% and if radian=3.14, the matching rate is 0%.

Next, the calculating unit 3 calculates magnitudes of the space vectors X and Y. The magnitudes of the space vectors X and Y can be obtained by the following equation.

$$|X| = \sqrt{(a1)^2 + (a2)^2 + (a3)^2}$$

$$|Y| = \sqrt{(b1)^2 + (b2)^2 + (b3)^2} \quad \text{[Equation 2]}$$

From the calculated magnitudes of the space vectors X and Y, the calculating unit 3 calculates a matching rate (ratio) by percentage of magnitudes (vector magnitudes) of the electrocardiogram waveform A and the electrocardiogram waveform B by the following equation.

If $|X| \leq |Y|$, Matching rate=$|X| \div |Y| \times 100$. [Equation 3]

If $|X| > |Y|$, Matching rate=$|Y| \div |X| \times 100$.

Then, based on the directions and magnitudes of the vectors, the calculating unit 3 calculates a matching rate of the electrocardiogram waveform A and the electrocardiogram waveform B by the following equation. Although an arithmetic average of the matching rate of the vector directions and the matching rate of the vector magnitudes is obtained in the following equation, a weighted average may be obtained while changing a weighting of each matching rate.

(Matching rate of vector directions+Matching rate of vector magnitudes)$\div 2[\%]$ [Equation 4]

Meanwhile, in this example, the matching rate is calculated with respect to the electrocardiogram waveform A and the electrocardiogram waveform B, each of which is one of the standard 12-lead electrocardiogram waveforms as described above, but in practice, matching rates are respectively calculated with respect to all of the standard 12-lead electrocardiogram waveforms.

However, conventionally, when deciding a matching rate of biometric waveforms, only a matching rate of vector directions obtained by space-vectorization of waveforms, i.e., a matching rate of shapes of waveforms has been mostly calculated and decided. For this reason, for example, when waveforms, such as waveforms having a similar shape but a different magnitude, are similar to each other only in shape, a calculated matching rate has a higher value. Accordingly, even when an electrocardiogram waveform measured by pacing and an electrocardiogram waveform actually measured due to a premature ventricular contraction are similar to each other only in shape, the matching rate has a higher value to decrease reliability, and as a result, it is difficult to identify an exact occurrence origin thereof.

Contrarily, according to the bio-information analysis device 1 of the present embodiment, magnitudes (vector magnitudes) of the electrocardiogram waveforms A and B as well as shapes (vector directions) of the electrocardiogram waveforms A and B are used as indicators to calculate the matching rate of the electrocardiogram waveforms A and B. Accordingly, because reliability of the matching rate can be increased, an occurrence origin of the premature ventricular contraction can be exactly identified, thereby allowing an unnecessary cauterization (ablation) to be avoided and also a lesion to be surely cauterized.

Next, a method of calculating a matching rate of magnitudes of two electrocardiogram waveforms having different phases will be described with reference to FIGS. 3A and 3B.

Figure 3A:
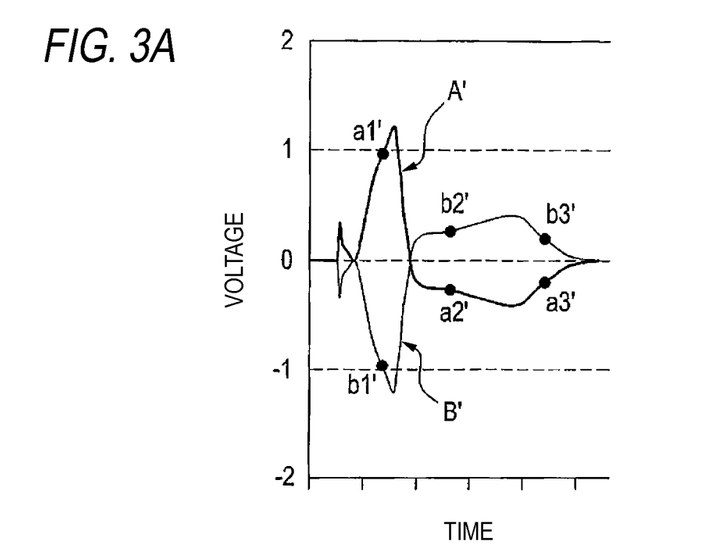
FIGS. 3A and 3B are views explaining a matching rate in magnitude of two electrocardiogram waveforms having different phases.

Waveforms in FIG. 3A is one which an electrocardiogram waveform A', which is measured when a premature ventricular contraction is actually occurred, and an electrocardiogram waveform B', which is induced by pacing and similar to an arrhythmia, are overlapped and displayed. The electrocardiogram waveforms B' has, at all sample points b1', b2' and b3' thereof, phases reversed relative to those at sample points a1', a2' and a3' of the electrocardiogram waveform A'.

When phases of the electrocardiogram waveform B' and phases of the electrocardiogram waveform A', from which a matching rate is to be calculated, are reversed relative to each other as described above, the calculating unit 3 calculates magnitudes of space vectors X1 and Y1 for calculating a matching rate of vector magnitudes as in the following equation.

$|X1| = \sqrt{(a1')^2 + (a2')^2 + (a3')^2}$ $|Y1| = \sqrt{(b1')^2 + (b2')^2 + (b3')^2} = \sqrt{0^2 + 0^2 + 0^2}$ [Equation 5]

Namely, the magnitude of the space vector X1 is calculated as described above, and the magnitude of the space vector Y1 is calculated, assuming that values of the sample points b1', b2' and b3' having reversed phases are zero (0).

Figure 3B:
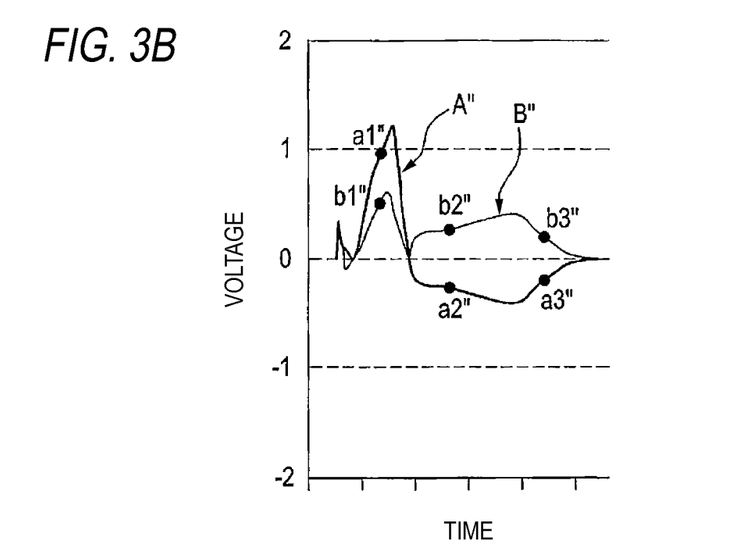

Waveforms in FIG. 3B is one which an electrocardiogram waveform A", which is measured when a premature ventricular contraction is actually occurred, and an electrocardiogram waveform B", which is induced by pacing and similar to an arrhythmia, are overlapped and displayed. The electrocardiogram waveforms B" has, at a sample point b1", the same phase as that at a sample point a1" of the electrocardiogram waveform A", but at sample points b2" and b3", phases reversed relative to those at sample points a2" and a3" of the electrocardiogram waveform A".

In this case, the calculating unit 3 calculates magnitudes of space vectors X2 and Y2 for calculating a matching rate of vector magnitudes as in the following equation.

$|X2| = \sqrt{(a1'')^2 + (a2'')^2 + (a3'')^2}$ $|Y2| = \sqrt{(b1'')^2 + (b2'')^2 + (b3'')^2} = \sqrt{(b1)^2 + 0^2 + 0^2}$ Namely, the magnitude of the space vector X2 is calculated as described above, and the magnitude of the space vector Y2 is calculated, assuming that values of the sample points b2" and b3" having reversed phases are zero (0).

In this way, when the phases of the electrocardiogram waveforms B' and B", which are induced by pacing and similar to an arrhythmia, are reversed relative to the phases of the electrocardiogram waveform A' and A" when a premature ventricular contraction is actually occurred, a correction in which magnitudes of portions having reversed phases is assumed to zero is performed in calculating a matching rate of magnitudes of waveforms. Therefore, reliability of the calculated matching rate can be further increased and an occurrence origin of the premature ventricular contraction can be exactly identified.

Figure 4A:
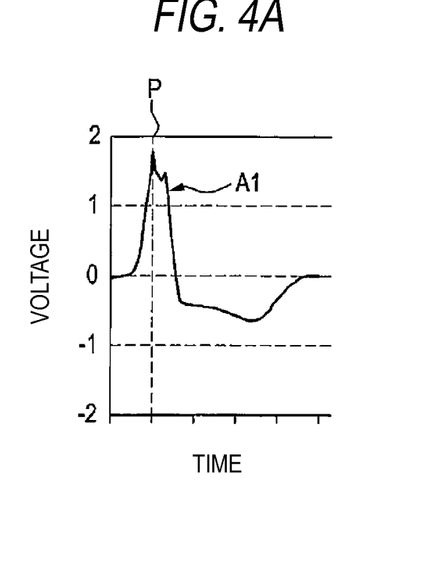
FIGS. 4A to 4C are views explaining a location where two electrocardiogram waveforms are overlapped.
Figure 4B:
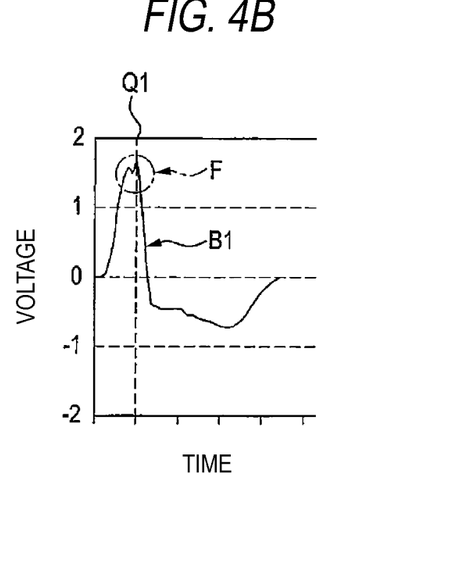

Then, locations where two electrocardiogram waveforms are overlapped will be described with reference to FIG. 4. A waveform in FIG. 4A is an electrocardiogram waveform A1 measured when a premature ventricular contraction is actually occurred, and a location of a point P on the electrocardiogram waveform A1 represents a top point having the maximum amplitude within a QRS interval of the waveform. A waveform in FIG. 4B is an electrocardiogram waveform B1, which is induced by pacing and similar to an arrhythmia, and a location of a point Q on the electrocardiogram waveform B1 represents a top point having the maximum amplitude within a QRS interval of the waveform.

Figure 4C:
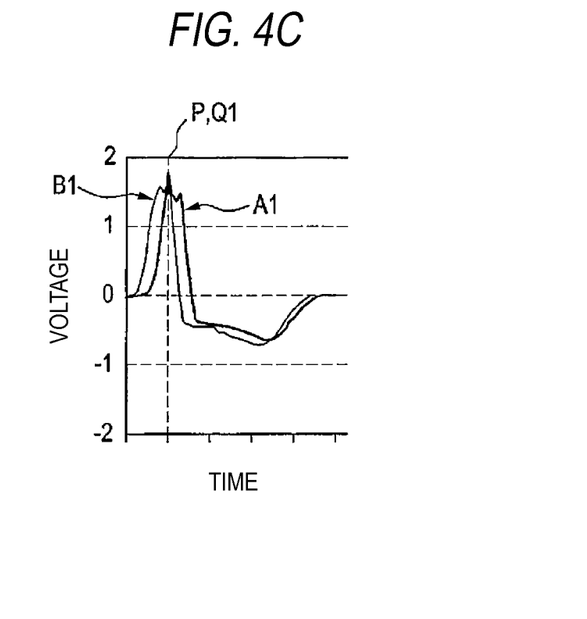

When calculating a matching rate of the electrocardiogram waveform A1 and the electrocardiogram waveform B1, the calculating unit 3 defines the location of the point P, which is the top point in the electrocardiogram waveform A1, as a reference point P for overlapping. Also, the calculating unit 3 defines the location of the point Q, which is the top point in the electrocardiogram waveform B1, as a temporary reference point Q1 for overlapping. Then, a matching rate of the electrocardiogram waveform A1 and the electrocardiogram waveform B1 when the reference point P and the temporary reference point Q1 are overlapped with each other as shown in FIG. 4C is first calculated.

Figure 5A:
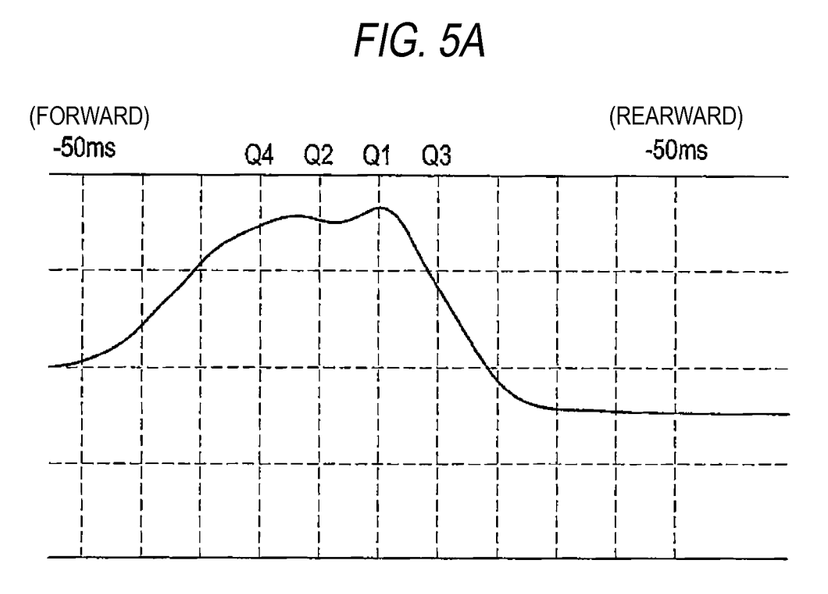
FIGS. 5A and 5B are views explaining a location where two electrocardiogram waveforms are overlapped.

Subsequently, the calculating unit 3 calculates a matching rate of the electrocardiogram waveform A1 and the electrocardiogram waveform B1 while moving a location of the reference point on the electrocardiogram waveform B1 from the location of the temporary reference point Q1 in forward and rearward directions on a time axis. FIG. 5A shows an enlarged view of a broken-line area F in the electrocardiogram waveform B1 shown in FIG. 4B. As shown in FIG. 5A, the calculating unit 3 moves the location of the reference point from the temporary reference point Q1 in forward and rearward directions by intervals of 10 msec. Then, the calculating unit 3 defines a location of a point Q2 and a location of a point Q2, which are moved from the temporary reference point Q1 in forward and rearward directions by 10 msec, as a temporary reference point Q2 and a temporary reference point Q3, respectively. The calculating unit 3 calculates matching rates of the electrocardiogram waveform A1 and the electrocardiogram waveform B1 when the reference point P of the electrocardiogram waveform A1 and the temporary reference point Q2 of the electrocardiogram waveform B1 are overlapped with each other and when the reference point P and the temporary reference point Q3 are overlapped with each other.

In addition, the calculating unit 3 performs calculation of each of the above matching rates with respect to all of the standard 12-lead electrocardiogram waveforms in the same order as described above.

The calculating unit 3 calculates average matching rates of matching rates of the standard 12-lead electrocardiogram waveforms calculated by overlapping each of the temporary reference points Q1, Q2 and Q3 and finds a temporary reference point at which the highest average matching rate is exhibited. Then, for example, when the average matching rates at the temporary reference points Q1, Q2 and Q3 have a relationship of Q2>Q1>Q3, the reference point Q is assumed to be located more forward on the time axis than the temporary reference point Q1 and thus the calculating unit 3 additionally finds a location of the reference point Q for overlapping the electrocardiogram waveform B1 as described below.

The calculating unit 3 defines a location of a point Q4, which is moved from the temporary reference point Q2 in the forward direction on the time axis by 10 msec, as a temporary reference point Q4 and then calculates a matching rate of the electrocardiogram waveform A1 and the electrocardiogram waveform B1 when the reference point P of the electrocardiogram waveform A1 and the temporary reference point Q4 of the electrocardiogram waveform B1 are overlapped with each other. In the same manner, the calculating unit 3 also calculates matching rates of other electrocardiogram waveforms in the standard 12-lead electrocardiogram waveforms, and then calculates an average matching rate of the matching rates of the standard 12-lead electrocardiogram waveforms. If the calculated average matching rate has a relationship of, for example, Q2>Q4, the reference point Q is assumed to be located between the temporary reference point Q2 and the temporary reference point Q4, and thus the calculating unit 3 additionally finds a location of the reference point Q for overlapping between the temporary reference points Q2 and Q4.

Figure 5B:
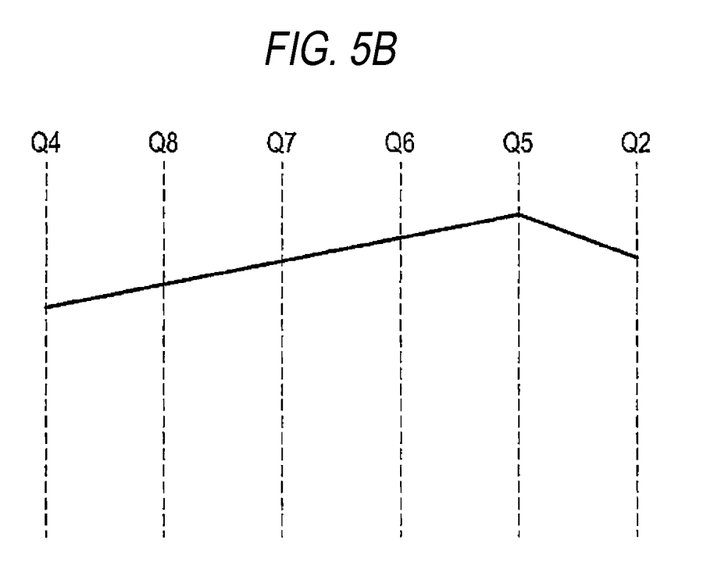

FIG. 5B shows an enlarged view between the temporary reference points Q2 and Q4 the electrocardiogram waveform B1 shown in FIG. 5A. As shown in FIG. 5B, the calculating unit 3 equally divides between the temporary reference points Q2 and Q4 (e.g., five equal division) and then defines temporary reference points Q5 to Q8. Also, the calculating unit 3 overlaps each of the temporary reference points Q5 to Q8 with the reference point P1 of the electrocardiogram waveform A1 and then calculates a matching rate in each case. In the same manner, the calculating unit 3 also calculates matching rates of other electrocardiogram waveforms in the standard 12-lead electrocardiogram waveforms, and then calculates average matching rates of the matching rates of the standard 12-lead electrocardiogram waveforms. The calculating unit 3 finds a temporary reference point, at which the highest average matching rate of the calculated average matching rates is exhibited, and then defines a location of the temporary reference point as the reference point Q for overlapping the electrocardiogram waveform B1 with respect to the reference point P of the electrocardiogram waveform A1.

In this way, upon calculation of the matching rate, when the electrocardiogram waveform B1, which is induced by pacing and similar to an arrhythmia, is overlapped with the electrocardiogram waveform A1, which is measured when a premature ventricular contraction is actually occurred, the reference point of the electrocardiogram waveform B1 at which the highest average matching rate in the standard 12-lead electrocardiogram waveforms is exhibited, is obtained. Accordingly, because the optimal reference point for overlapping can be obtained, a matching rate having a higher reliability can be calculated and an occurrence origin of the premature ventricular contraction can be exactly identified.

Then, a correction of an electrocardiogram waveform, which is induced by pacing and similar to an arrhythmia, will be described with reference to FIG. 6. Waveforms in FIG. 6 show an electrocardiogram waveform B2, which is induced by pacing and similar to an arrhythmia, and a pulse signal K outputted from the electrical stimulation generating unit 4.

Figure 6:
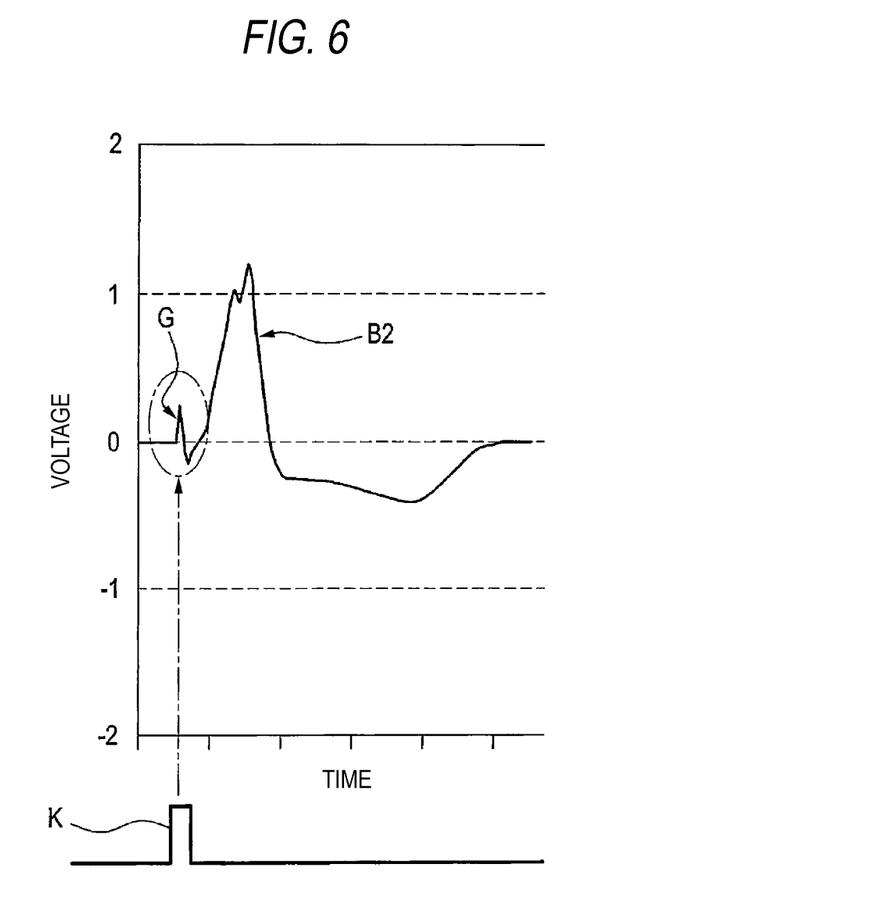
FIG. 6 is a view explaining correction of an electrocardiogram waveform of an arrhythmia induced by pacing.

As shown in FIG. 6, the electrocardiogram waveform B2 has a stimulation potential component G, as shown in a broken-line area, generated synchronizing with the pulse signal K. As described above, the pulse signal K is inputted from the electrical stimulation generating unit 4 to the measuring unit 2, synchronizing with the electrical stimulation signal for performing pacing. The calculating unit 3 estimates the stimulation potential component G in the electrocardiogram waveform B2 based on the pulse signal K inputted to the measuring unit 2 and then performs calculation of the matching rate, excluding the stimulation potential component G from the electrocardiogram waveform B2.

The bio-information analysis device 1 repeatedly performs pacing based on operations of calculating the matching rate as described above, and then specifies a site, at which an electrocardiogram waveform having a higher matching rate is detected, and identifies the site as an occurrence origin of the premature ventricular contraction.

The display control unit 5 allows the display 6 to display electrocardiogram waveforms, which are measured when a premature ventricular contraction is actually occurred, electrocardiogram waveforms, which are measured when waveforms similar to an arrhythmia are artificially occurred by pacing, a calculated matching rate of the electrocardiogram waveforms, a site identified as an occurrence origin of the premature ventricular contraction and the like.

In this way, upon calculation of the matching rate, the stimulation potential component G generated synchronizing with the pulse signal K in the electrocardiogram waveform B2, which is induced by pacing and similar to an arrhythmia, is excluded. Accordingly, the electrocardiogram waveform B2 can be corrected to be further similar to an electrocardiogram waveform actually occurred due to a premature ventricular contraction, a matching rate having a higher reliability can be calculated and an occurrence origin of the premature ventricular contraction can be exactly identified.

Next, calculation of a matching rate in a case where a premature ventricular contractions are originated from a tricuspid annulus and also a case where premature ventricular contractions are originated from a right ventricular outflow tract (RVOT) will be described.

The premature ventricular contractions originated from the tricuspid annulus include a premature ventricular contraction originated from a free wall and a premature ventricular contraction originated from a septum. Electrocardiogram waveforms originated from the free wall and electrocardiogram waveforms originated from the septum are similar in shape, except that the electrocardiogram waveforms originated from the free wall have deeper S-waves in V1 to V3 lead waveforms of the chest lead waveforms than those of the electrocardiogram waveforms originated from the septum. For this reason, a matching rate of shapes of the electrocardiogram waveforms is relatively higher. However, a matching rate of magnitudes of the electrocardiogram waveform is likely to have a lower value.

The premature ventricular contractions originated from RVOT are similar in shape of the electrocardiogram waveforms even if occurrence locations thereof are different in terms of a height within the outflow tract, and thus a matching rate of shape thereof is very high. However, there is a difference in magnitude of the electrocardiogram waveforms. Specifically, electrocardiogram waveforms originated from a pulmonary artery side of RVOT have a feature that wave heights in II, III and aVF lead waveforms of the lime lead waveforms thereof are higher than those of electrocardiogram waveforms originated from an inlet portion of RVOT.

When having such a feature, magnitudes of the electrocardiogram waveforms as well as shapes thereof can be employed as indicators upon calculation of a matching rate of the electrocardiogram waveforms, thereby increasing reliability of a matching rate. In addition, upon calculation of the matching rate of the electrocardiogram waveforms, the matching rate may be calculated by weighting any lead electrocardiogram waveforms, which exhibit a characteristic portion, of the standard 12-lead electrocardiogram waveforms.

For example, in the case of premature ventricular contractions originated from the tricuspid annulus, calculation results of matching rates of electrocardiogram waveforms in V1 to V3 lead may have precedence in identifying occurrence origins of the premature ventricular contractions. Also, in the case of the premature ventricular contractions originated from RVOT, calculation results of matching rates of electrocardiogram waveforms in II, III and aVF lead waveforms may have precedence in identifying occurrence origins of the premature ventricular contractions.

Meanwhile, the presently disclosed subject matter is not limited to the foregoing embodiments, but appropriate changes, modifications or the like thereof can be made. In addition, material, shape, dimension, number, installation position and the like of each of the components of the foregoing embodiments are not limited but arbitrary as long as the presently disclosed subject matter can be achieved.

For example, an arrhythmia to be applied may include a tachyarrhythmia, such as paroxysmal supraventricular tachycardia, atrial tachycardia, auricular flutter and paroxysmal ventricular tachycardia.

What is claimed is:

1. A bio-information analysis device, comprising:
   a measuring unit that measures a first shape and a second magnitude of a first biometric waveform of a subject and a second shape and a second magnitude of a second biometric waveform of the subject; and
   a calculating unit that calculates a similarity rate between the first biometric waveform and the second biometric waveform based on angles formed by first and second space vectors calculated from the first biometric waveform and the second biometric waveform measured by the measuring unit and the magnitudes of the space vectors.

2. The bio-information analysis device according to claim 1, wherein the first biometric waveform and the second biometric waveform are electrocardiogram waveforms.

3. The bio-information analysis device according to claim 2, wherein the first biometric waveform includes a waveform measured when a premature ventricular contraction is occurred and the second biometric waveform includes a waveform measured when a waveform is artificially occurred by pacing.

4. The bio-information analysis device according to claim 3, wherein when calculating the similarity rate between the first biometric waveform and the second biometric waveform, the similarity rate is calculated in such a manner that a point, at which a highest similarity rate is exhibited, of points on the second biometric waveform is overlapped with a highest amplitude point of the first biometric waveform.

5. The bio-information analysis device according to claim 3, wherein when calculating the similarity rate, a stimulation potential waveform component, which is generated upon pacing, of the second biometric waveform is excluded.

6. The bio-information analysis device according to claim 4, wherein when calculating the similarity rate, a stimulation potential waveform component, which is generated upon pacing, of the second biometric waveform is excluded.

7. The bio-information analysis device according to claim 3, wherein upon calculation of a similarity rate with respect to magnitudes of the first biometric waveform and the second biometric waveform, a magnitude of a portion having a phase reversed relative to that of the first biometric waveform, of the second biometric waveform, is changed to zero.

8. The bio-information analysis device according to claim 4, wherein upon calculation of a similarity rate with respect to magnitudes of the first biometric waveform and the second biometric waveform, a magnitude of a portion having a phase reversed relative to that of the first biometric waveform, of the second biometric waveform, is changed to zero.

9. The bio-information analysis device according to claim 5, wherein upon calculation of a similarity rate with respect to magnitudes of the first biometric waveform and the second biometric waveform, a magnitude of a portion having a phase reversed relative to that of the first biometric waveform, of the second biometric waveform, is changed to zero.

10. The bio-information analysis device according to claim 6, wherein upon calculation of a similarity rate with respect to magnitudes of the first biometric waveform and the second biometric waveform, a magnitude of a portion having a phase reversed relative to that of the first biometric waveform, of the second biometric waveform, is changed to zero.

11. A bio-information analysis device, comprising:
a measuring unit that measures a first shape and a first magnitude of a first biometric waveform of a subject and a second shape and a second magnitude of a second biometric waveform of the subject; and
a calculating unit that calculates a similarity rate between the first biometric waveform and the second biometric waveform based on the shapes and the magnitudes of the first biometric waveform and the second biometric waveform measured by the measuring unit,
wherein the first biometric waveform and the second biometric waveform are electrocardiogram waveforms,
wherein the first biometric waveform includes a waveform measured when a premature ventricular contraction is occurred and the second biometric waveform includes a waveform measured when a waveform is artificially occurred by pacing, and
wherein when calculating the similarity rate, a stimulation potential waveform component, which is generated upon pacing, of the second biometric waveform is excluded.

12. A bio-information analysis device, comprising:
a measuring unit that measures a first shape and a first magnitude of a first biometric waveform of a subject and a second shape and a second magnitude of a second biometric waveform of the subject; and
a calculating unit that calculates a similarity rate between the first biometric waveform and the second biometric waveform based on the shapes and the magnitudes of the first biometric waveform and the second biometric waveform measured by the measuring unit,
wherein the first biometric waveform and the second biometric waveform are electrocardiogram waveforms,
wherein the first biometric waveform includes a waveform measured when a premature ventricular contraction is occurred and a second biometric waveform includes a waveform measured when a waveform is artificially occurred by pacing,
wherein when calculating the similarity rate between the first waveform and the second waveform, the similarity rate is calculated in such a manner that a point, at which a highest similarity rate is exhibited, of points on the second biometric waveform is overlapped with a highest amplitude point of the first biometric waveform, and
wherein when calculating the similarity rate, a stimulation potential waveform component, which is generated upon pacing, of the second biometric waveform is excluded.

* * * * *